(12) United States Patent
Yoshino et al.

(10) Patent No.: US 11,602,620 B2
(45) Date of Patent: Mar. 14, 2023

(54) DILATOR, TREATMENT SYSTEM AND DILATING METHOD

(71) Applicant: OLYMPUS CORPORATION, Tokyo (JP)

(72) Inventors: Masahiro Yoshino, Machida (JP); Yuji Sakai, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 203 days.

(21) Appl. No.: 16/838,058

(22) Filed: Apr. 2, 2020

(65) Prior Publication Data

US 2020/0282193 A1    Sep. 10, 2020

Related U.S. Application Data

(63) Continuation of application No. PCT/JP2017/036503, filed on Oct. 6, 2017.

(51) Int. Cl.
*A61M 29/00* (2006.01)
*A61B 17/24* (2006.01)
*A61B 17/00* (2006.01)

(52) U.S. Cl.
CPC ............. *A61M 29/00* (2013.01); *A61B 17/24* (2013.01); *A61B 2017/00477* (2013.01); *A61M 2210/0618* (2013.01)

(58) Field of Classification Search
CPC .......... A61M 29/00; A61M 2210/0618; A61B 17/24; A61B 17/1688; A61B 2017/00477; A61B 2017/2926; A61B 2017/2927; A61B 2017/2929; A61B 2017/2932; A61B 17/8858; A61B 17/0206; A61B 17/0231;

(Continued)

(56) References Cited

U.S. PATENT DOCUMENTS

| 7,740,642 B2 | 6/2010 | Becker |
| 2007/0073269 A1* | 3/2007 | Becker ............... A61M 3/0295 604/509 |

(Continued)

FOREIGN PATENT DOCUMENTS

JP    2003-509169 A    3/2003

OTHER PUBLICATIONS

English translation of International Preliminary Report on Patentability dated Apr. 8, 2020 together with the Written Dpinion received in related International Application No. PCT/JP2017/036503.

(Continued)

*Primary Examiner* — Katherine H Schwiker
(74) *Attorney, Agent, or Firm* — Scully, Scott, Murphy & Presser, P.C.

(57) ABSTRACT

A dilator, dilating a narrowed part of a paranasal sinus, includes an end effector, and the end effector includes a pair of treatment pieces openable and closable relative to each other. Each of the treatment pieces includes a treatment surface facing a side on which the treatment piece opens, and each of the treatment surfaces includes an inclined surface inclined to be closer to a side on which the treatment piece closes as a distance to a distal end of the treatment piece decreases. The pair of inclined surfaces become parallel or substantially parallel to each other when the treatment pieces are opened to a maximum angle. The end effector opens anisotropically.

21 Claims, 11 Drawing Sheets

(58) Field of Classification Search
CPC ... A61B 17/02; A61B 17/0218; A61B 17/025; A61B 2017/0256–0275
See application file for complete search history.

(56) References Cited

U.S. PATENT DOCUMENTS

| | | | |
|---|---|---|---|
| 2007/0250100 A1 | 10/2007 | Schon et al. | |
| 2010/0121153 A1* | 5/2010 | To .................... | A61B 17/3417 600/214 |
| 2010/0274275 A1* | 10/2010 | Stammberger ..... | A61B 17/1688 606/198 |
| 2014/0051936 A1* | 2/2014 | Newcomb .............. | A61B 17/02 606/1 |
| 2015/0250992 A1* | 9/2015 | Morriss ............. | A61M 25/0074 606/198 |
| 2016/0249796 A1* | 9/2016 | Fujisaki ................. | A61M 1/84 600/114 |

OTHER PUBLICATIONS

International Search Report dated Dec. 19, 2017 issued in International Application No. PCT/JP2017/036503.

* cited by examiner

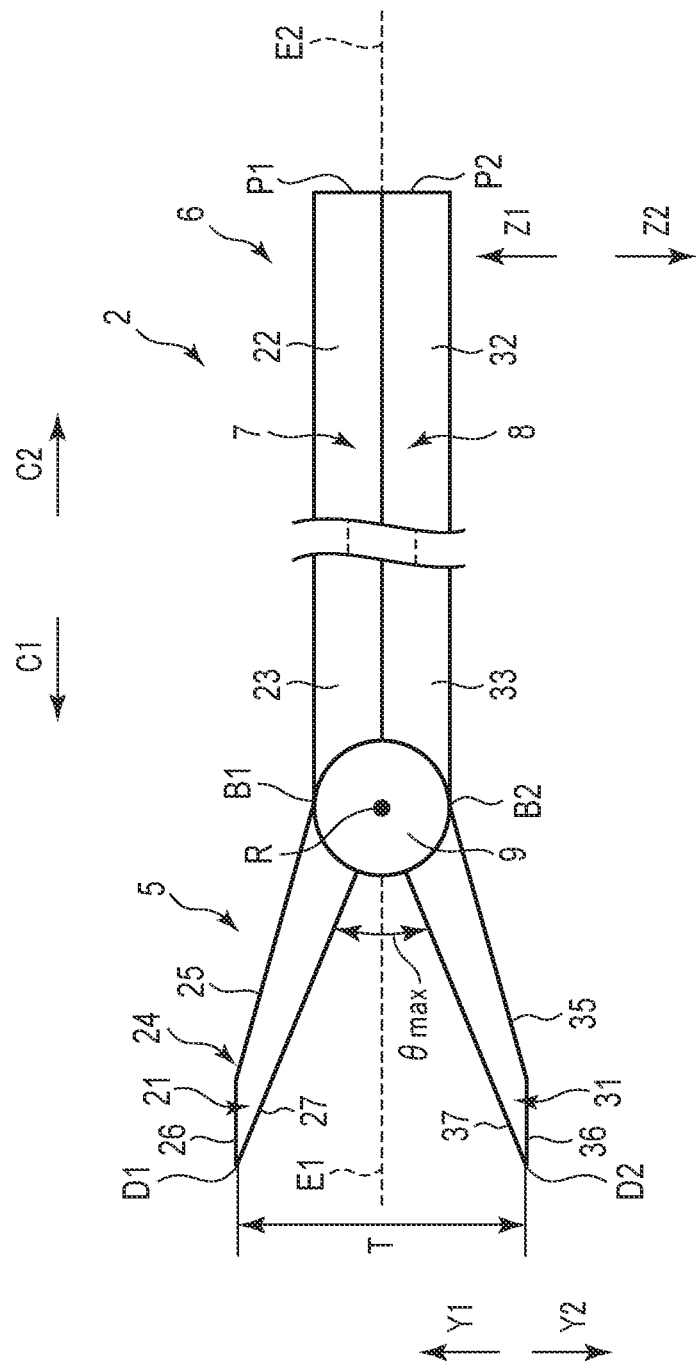
F I G. 14

US 11,602,620 B2

DILATOR, TREATMENT SYSTEM AND DILATING METHOD

CROSS-REFERENCE TO RELATED APPLICATIONS

This is a Continuation Application of PCT Application No. PCT/JP2017/036503, filed Oct. 6, 2017, the entire contents of which are incorporated herein by reference.

BACKGROUND OF THE INVENTION

1. Field of the Invention

The present invention relates to a dilator configured to dilate a narrowed part of the paranasal sinuses, and a treatment system including the dilator. The present invention relates to a dilating method performed by using the dilator.

2. Description of the Related Art

U.S. Pat. No. 7,740,642B2 discloses a dilator configured to dilate a narrowed part of the paranasal sinuses. This dilator includes a balloon, and the balloon is disposed in the narrowed part in a deflated state during the dilation of the narrowed part. The balloon is inflated in the narrowed part of the paranasal sinuses, causing the narrowed part to be dilated by pressure from the balloon. At this time, the balloon expands isotropically toward the outer peripheral side, and the narrowed part is isotropically dilated toward the outer peripheral side of the balloon.

BRIEF SUMMARY OF THE INVENTION

According to one aspect of the invention, a dilator that dilates a narrowed part of a paranasal sinus, the dilator including: an end effector extending along an extension axis from a proximal side toward a distal side, and including a first treatment piece and a second treatment piece that is openable and closable relative to the first treatment piece; a first treatment surface provided in the first treatment piece and facing a side on which the first treatment piece opens; a second treatment surface provided in the second treatment piece and facing a side on which the second treatment piece opens; a first inclined surface provided on the first treatment surface, and inclined to be closer to a side on which the first treatment piece closes as a distance to a distal end of the first treatment piece decreases; and a second inclined surface provided on the second treatment surface, and inclined to be closer to a side on which the second treatment piece closes as a distance to a distal end of the second treatment piece decreases, and the second inclined surface becoming parallel or substantially parallel to the first inclined surface when the first treatment piece and the second treatment piece are opened to a maximum angle relative to each other, wherein the end effector is configured to open anisotropically.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 14 is a schematic diagram showing the dilator according to the second modification in a state in which the treatment pieces are opened to a maximum angle.

DETAILED DESCRIPTION OF THE INVENTION

First Embodiment

A first embodiment of the present invention will be described with reference to FIGS. 1 to 10.

Figure 1:
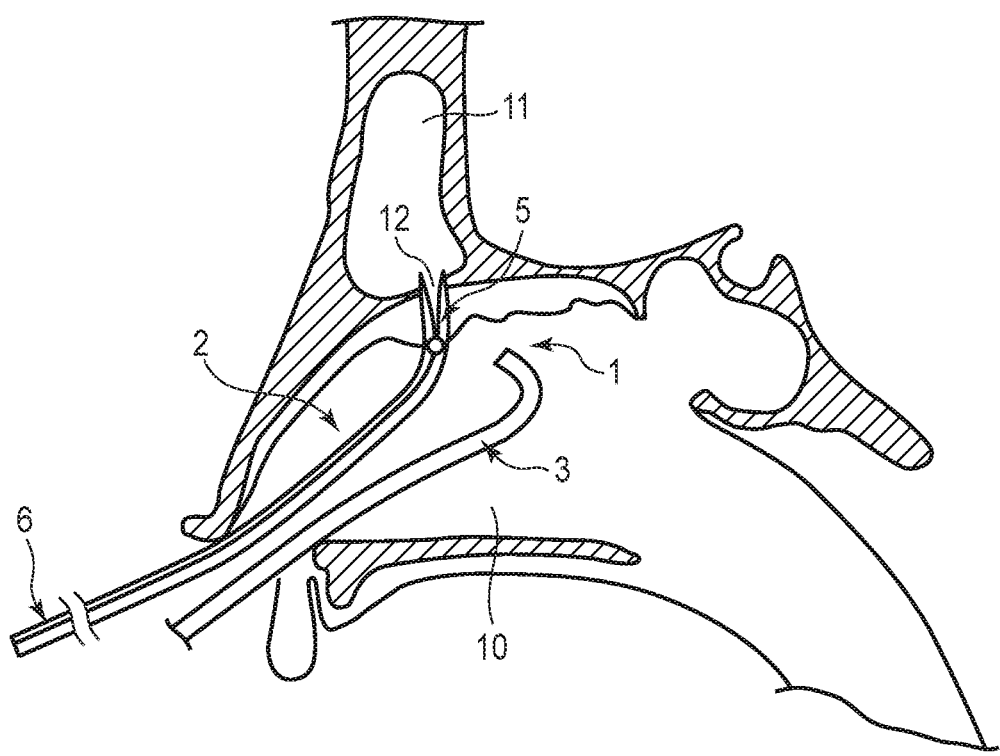
FIG. 1 is a schematic diagram showing an example of a state in which a treatment is being performed using a treatment system according to a first embodiment.

FIG. 1 is a diagram showing an example of a state in which a treatment is being performed using a treatment system 1 according to the present embodiment. As shown in FIG. 1, the treatment system 1 includes a dilator 2 as a dilating instrument, and an endoscope 3 as an observation apparatus. The dilator 2 includes an end effector 5 and an operating section 6. During the treatment, the end effector 5 is allowed to pass through a nasal cavity 10, and is disposed at a narrowed part (e.g., 12) of a paranasal sinus (e.g., 11). In the state of FIG. 1, the end effector 5 is disposed in a nasofrontal duct 12 between the nasal cavity 10 and frontal sinuses 11, which are one of the paranasal sinuses. During the treatment, the narrowed part (e.g., 12) of the paranasal sinus (e.g., 11) is dilated by the end effector 5. During the treatment, a distal portion of the endoscope 3 is inserted into the nasal cavity 10, and an image of the dilated narrowed part (e.g., 12) is captured by, for example, an imaging element (not illustrated), such as a CCD. That is, the endoscope 3 allows for observation of the narrowed part (e.g., 12) from the side of the nasal cavity 10. In an embodiment, observation of the narrowed part (e.g., 12) is performed using, as an observation apparatus, an apparatus that generates an image based on magnetic resonance imaging (MRI) or computed tomography (CT) scanning, instead of the endoscope 3.

Figure 2:
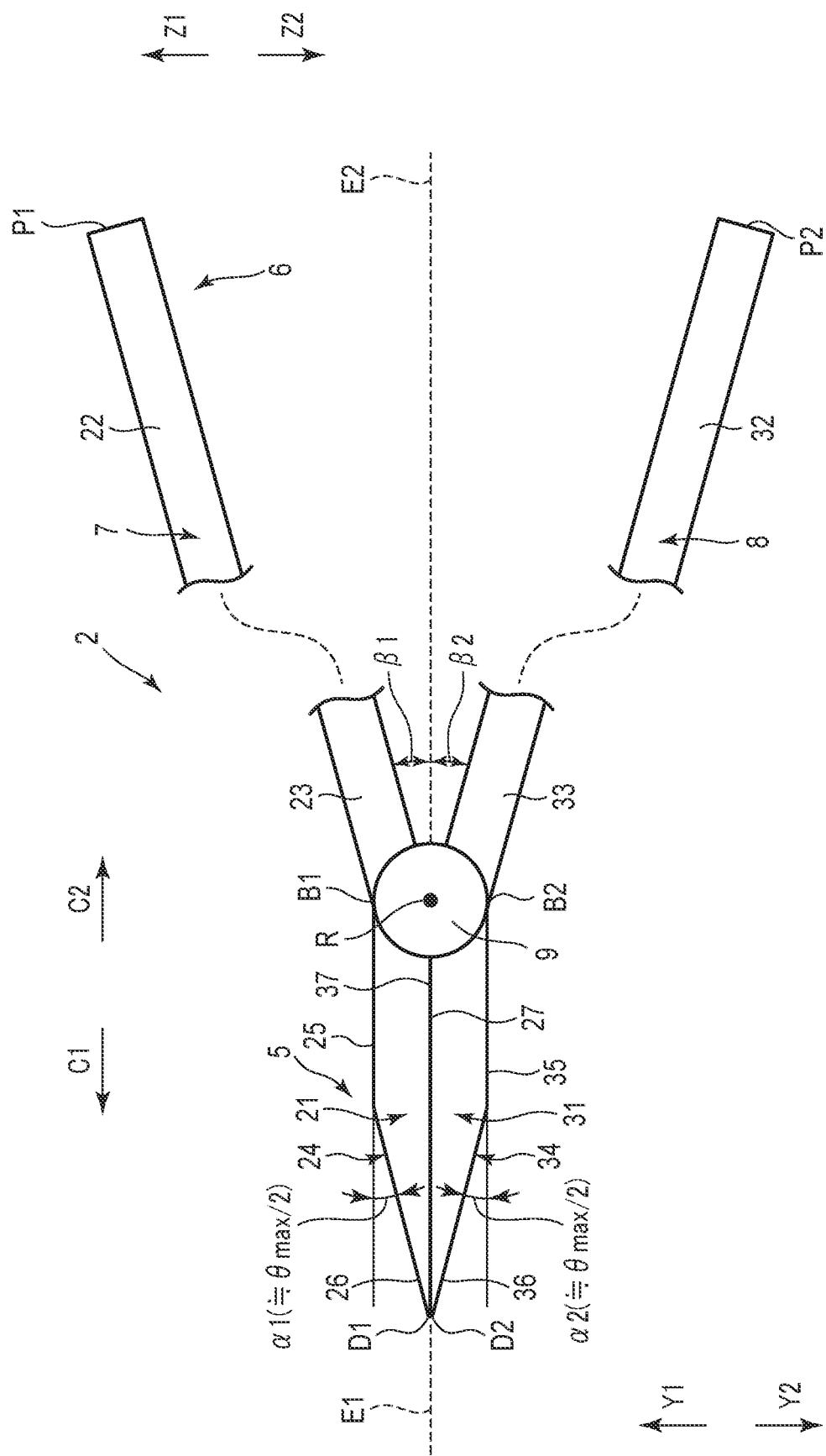
FIG. 2 is a schematic diagram showing a dilator according to the first embodiment in a state in which treatment pieces are closed to a minimum angle.
Figure 3:
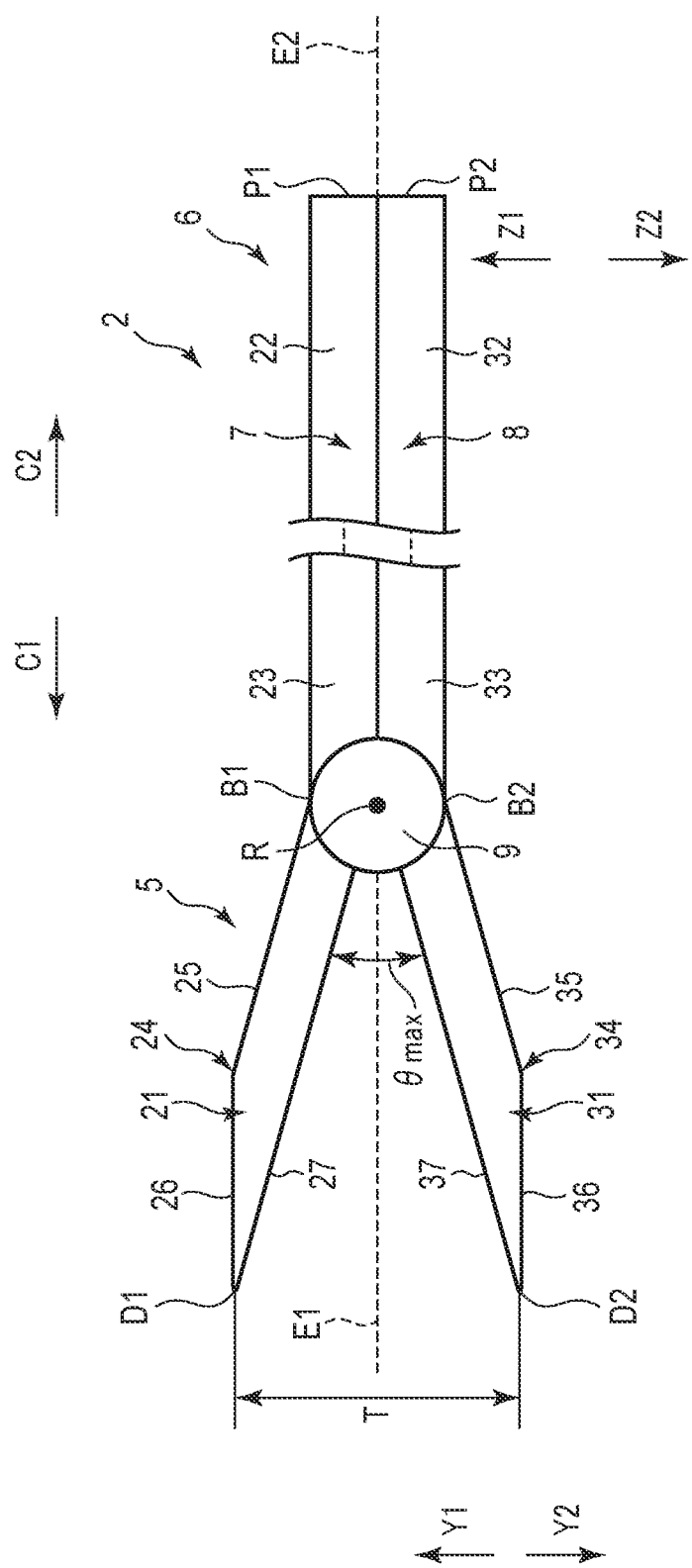
FIG. 3 is a schematic view showing the dilator according to the first embodiment in a state in which the treatment pieces are opened to a maximum angle.

FIGS. 2 and 3 are diagrams showing a configuration of the dilator 2. Let us assume that, in the dilator 2, the side on which the end effector 5 is located is a distal side (the side of an arrow C1), and the side on which the operating section (holder) 6 is located is a proximal side (the side of an arrow C2). As shown in FIGS. 2 and 3, the dilator 2 includes a first shaft 7 and a second shaft 8. The shafts 7 and 8 extend from the proximal side toward the distal side in the dilator 2. In the dilator 2, the shafts 7 and 8 are coupled via a coupling member (coupling) 9 such as a pin. In the present embodiment, the shafts 7 and 8 pivotally move relative to each other about a central axis R of the coupling member 9. The operating section 6 is provided proximal to the coupling member 9, and is located farther from the end effector 5 than the coupling member 9. Accordingly, the coupling member 9, which couples the shafts 7 and 8, is provided between the end effector 5 and the operating section 6.

The first shaft 7 includes a first treatment piece 21 forming the end effector 5, and a first grip 22 forming the operating section 6. In the present embodiment, the first treatment piece 21 forms a distal end D1 of the first shaft 7, and the first grip 22 forms a proximal end P1 of the first shaft 7. In the first shaft 7, a first relay 23 extends continuously between the first treatment piece 21 and the first grip 22. Similarly, the second shaft 8 includes a second treatment piece 31 forming the end effector 5, and a second grip 32 forming the operating section 6. In the present embodiment, the second treatment piece 31 forms a distal end D2 of the second shaft 8, and the second grip 32 forms a proximal end P2 of the second shaft 8. In the second shaft 8, a second relay 33 extends continuously between the second treatment piece 31 and the second grip 32. In the present embodiment, the first relay is connected to the second relay 33 via the coupling member 9. That is, the coupling member 9 is attached to the relays 23 and 33.

Figure 4:
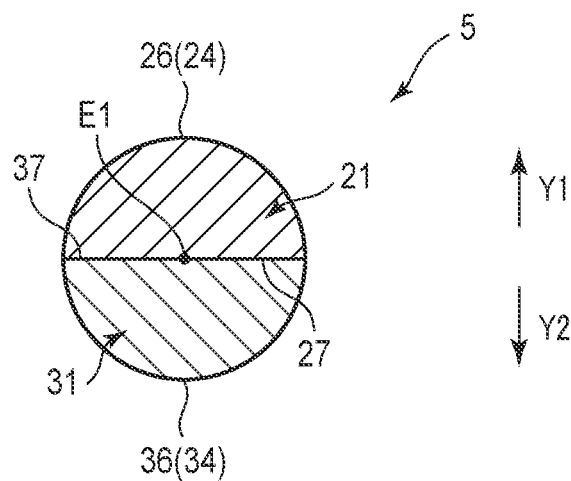
FIG. 4 is a cross-sectional view schematically showing an end effector according to the first embodiment in a state in which treatment pieces are closed to the minimum angle, as viewed in a cross section perpendicular or substantially perpendicular to an extension axis passing through an inclined surface.
Figure 5:
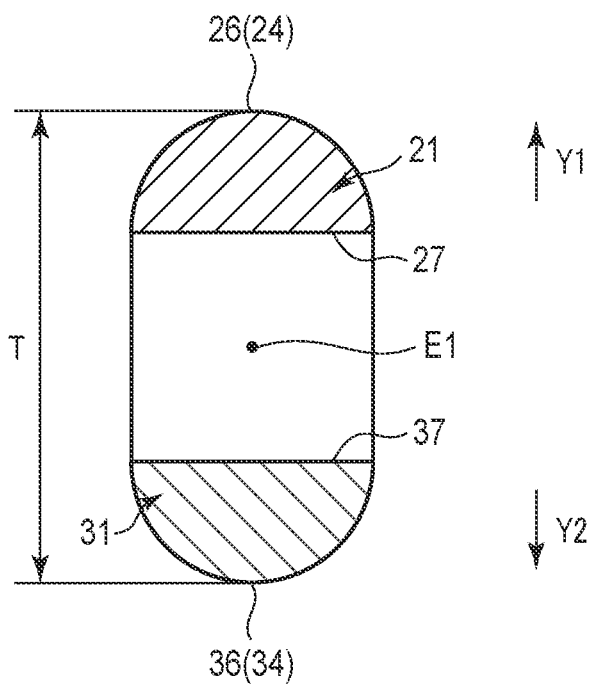
FIG. 5 is a cross-sectional view schematically showing the end effector according to the first embodiment in a state in which the treatment pieces are opened to the maximum angle, as viewed in a cross section perpendicular or substantially perpendicular to an extension axis passing through an inclined surface.

FIGS. 4 and 5 are views showing the end effector 5. As shown in FIGS. 2 to 5, the end effector 5 includes an extension axis E1 as a central axis, and extends from the proximal side toward the distal side along an extension axis E1. In the examples of FIGS. 2 to 5, the extension axis E1 is straight or substantially straight; however, the extension axis E1 may be bent in another embodiment. In the end effector 5, the treatment pieces 21 and 31 are disposed on sides opposite to each other, with the extension axis E1 interposed therebetween. As the shafts 7 and 8 pivot about the central axis R of the coupling member 9, the treatment pieces 21 and 31 are opened or closed relative to each other. That is, the treatment pieces 21 and 31 are coupled to each other via the coupling member 9 so as to be openable and closable relative to each other. The direction in which the end effector 5 opens and closes (the direction shown by the arrows Y1 and Y2) through a movement of opening and closing the treatment pieces 21 and 31 relative to each other intersect a direction along the extension axis E1 (in a perpendicular or substantially perpendicular manner), and intersect the direction along the central axis R of the coupling member 9 (in a perpendicular or substantially perpendicular manner). FIGS. 2 and 4 show a state in which the treatment pieces 21 and 31 are closed to a minimum angle, and FIGS. 3 and 5 show a state in which the treatment pieces 21 and 31 are opened to a maximum angle.

An outer surface of the first treatment piece 21 includes a first opposed surface 27 facing a side on which the first treatment piece 21 closes (the side of the arrow Y2), and an outer surface of the second treatment piece 31 includes a second opposed surface 37 facing a side on which the second treatment piece 31 closes (the side of the arrow Y1). The opposed surfaces 27 and 37 are opposed to each other. In the present embodiment, an angle formed by the opposed surfaces 27 and 37 is an opening angle $\theta$ between the treatment pieces 21 and 31. In the examples of FIGS. 2 to 5, both of the opposed surfaces 27 and 37 are planar. When the treatment pieces 21 and 31 are closed to the minimum angle relative to each other, the first opposed surface 27 of the first treatment piece 21 abuts the second opposed surface 37 of the second treatment piece 31, and the opening angle $\theta$ between the treatment pieces 21 and 31 becomes 0° or substantially 0°. In the example of FIGS. 2 to 5, both of the opposed surfaces 27 and 37 become parallel or substantially parallel to the extension axis E1 of the end effector 5 when the treatment pieces 21 and 31 are closed to the minimum angle relative to each other. When the treatment pieces 21 and 31 are opened to the maximum angle relative to each other, the opening angle $\theta$ between the treatment pieces 21 and 31 reaches a maximum opening angle $\theta$max.

The operating section 6 includes an extension axis E2 as a central axis, and extends from the proximal side toward the distal end side along the extension axis E2. Even though the extension axis E2 is straight or substantially straight in the example of FIGS. 2 to 5, the extension axis E2 may be bent in another embodiment. In the operating section 6, the grips 22 and 32 are disposed on sides opposite to each other, with the extension axis E2 interposed therebetween. As the shafts 7 and 8 pivot about the central axis R of the coupling member 9, the grips 22 and 32 are opened or closed relative to each other. That is, the grips 22 and 32 are coupled to each other via the coupling member 9 so that they are openable and closable. The direction in which the operating section 6 opens and closes (the direction shown by the arrows Z1 and Z2) through the movement of opening and closing the grips 22 and 32 relative to each other intersect a direction along the extension axis E2 (in a perpendicular or substantially perpendicular manner), and intersect the direction along the central axis R of the coupling member 9 (in a perpendicular or substantially perpendicular manner). In the present embodiment, the direction in which the operating section 6 opens and closes become parallel or substantially parallel to the direction in which the end effector 5 opens and closes.

An operation to open or close the treatment pieces 21 and 31 relative to each other is input via the operating section 6. At the time of the input of the operation via the operating section 6, an operation force to move (pivot) the first shaft 7 including the first treatment piece 21 is applied on the first grip 22, and an operation force to move (pivot) the second shaft 8 including the second treatment piece 31 is applied on the second grip 32. In the present embodiment, the treatment pieces 21 and 31 are opened relative to each other, as the grips 22 and 32 are closed relative to each other.

The first relay 23 includes a bent position B1 in the vicinity of the coupling member 9, and the second relay 33 includes a bent position B2 in the vicinity of the coupling member 9. The direction in which the first relay 23 (first shaft 7) extends changes at the bent position B1, and the direction in which the second relay 33 (second shaft 8) extends changes at the bent position B2. The first treatment piece 21 is provided on the distal side with respect to the bent position B1, and the first grip 22 is provided on the proximal side with respect to the bent position B1. The second treatment piece 31 is provided on the distal side with respect to the bent position B2, and the second grip 32 is provided on the proximal side with respect to the bent position B2. In the embodiment shown in FIGS. 2 to 5, the dilator 2 extends from the distal ends (D1 and D2) of the end effector 5 to the position at which the coupling member 9 is attached, along the extension axis E1 of the end effector 5. Both of the bent positions B1 and B2 are located at the same or substantially the same position as the coupling member 9, in the direction along the extension axis E1. In the embodiment shown in FIGS. 2 to 5, a bending angle $\beta 1$ of the first relay 23 at the bent position B1 is equal to or substantially equal to half of the maximum opening angle $\theta max$ between the treatment pieces 21 and 31, and a bending angle $\beta 2$ of the second relay 33 at the bent position B2 is equal to or substantially equal to half of the maximum opening angle $\theta max$ between the treatment pieces 21 and 31. However, when, for example, at least one of a projection in the first grip 22 projecting toward the second grip 32 or a projection in the second grip 32 projecting toward the first grip 22 is provided, the above-described relationship between each of the bending angles $\beta 1$ and $\beta 2$ and the maximum opening angle $\theta max$ need not be established.

In an embodiment, the first relay 23 includes one or more bent positions or curved portions in addition to the bent position B1, and/or the second relay 33 includes one or more bent positions or curved portions in addition to the bent position B2. In this case, in the first joint 23, each of the bent positions or curved portions other than the bent position B1 may be located on the distal side (on the side of the first treatment piece 21) with respect to the bent position B1, or on the proximal side (on the side of the first grip 22) with respect to the bent position B1. Similarly, in the second joint 33, each of the bent positions or curved portions other than the bent position B2 may be located on the distal side (on the side of the second treatment piece 31) with respect to the bent position B2, or on the proximal side (on the side of the second grip 32) with respect to the bent position B2. However, when the first relay 23 includes a bent position or curved portion in addition to the bent position B1, and/or the second joint 33 includes a bent position or curved portion in addition to the bent position B2, the end effector 5 extends along the extension axis E1, and the direction in which the end effector 5 opens and closes through the movement of opening and closing the treatment pieces 21 and 31 relative to each other intersect the direction along the extension axis E1 (in a perpendicular or substantially perpendicular manner), similarly to the embodiment shown in FIGS. 2 to 5.

Even when the first relay 23 includes one or more bent positions or surved portions in addition to the bent position B1, and/or the second relay 33 includes one or more bent positions or curved portions in addition to the bent position B2, it is preferable that the operating section 6 extend along the extension axis E2, and that the direction in which the operating section 6 opens and closes through the operation of opening and closing the grips 22 and 32 relative to each other intersect the direction along the extension axis E2 (in a perpendicular or substantially perpendicular manner), similarly to the embodiment shown in FIGS. 2 to 5. Also, it is preferable that the direction in which the operating section 6 opens and closes be parallel or substantially parallel to the direction in which the end effector 5 opens and closes, and that the treatment pieces 21 and 31 be opened relative to each other as the grips 22 and 32 are closed relative to each other, similarly to the embodiment shown in FIGS. 2 to 5.

As shown in FIGS. 2 to 5, the outer surface of the first treatment piece 21 includes a first treatment surface facing a side on which the first treatment piece 21 opens (the side of the arrow Y1), and the outer surface of the second treatment piece 31 includes a second treatment surface 34 facing a side on which the second treatment piece 31 opens (the side of the arrow Y2). In the present embodiment, the treatment surfaces 24 and 34 face sides opposite to each other. The first treatment surface 24 includes a first extension surface 25 and a first inclined surface 26, and the second treatment surface 34 includes a second extension surface 35 and a second inclined surface 36. FIGS. 4 and 5 show the end effector 5 in cross-sections perpendicular or substantially perpendicular to the extension axis E1 and passing through the inclined surfaces 26 and 36. In the present embodiment, a distal end of the first inclined surface 26 is located at a distal end D1 of the first shaft 7, and a distal end of the second inclined surface 36 is located at a distal end D2 of the second shaft 8. The first extension surface 25 is continuous with a proximal side of the first inclined surface 26, and the second extension surface 35 is continuous with a proximal side of the second inclined surface 36. In the present embodiment, the range of extension of the first inclined surface 26 is identical or substantially identical to the range of extension of the second inclined surface 36, in the direction along the extension axis E1 of the end effector 5. If the range of extension of the first inclined surface 26 and the range of extension of the second inclined surface 36 overlap at least in part in the direction along the extension axis E1 of the end effector 5, the range of extension of the first inclined surface 26 may be deviated from the range of extension of the second inclined surface 36, in the direction along the extension axis E1.

In the example of FIGS. 2 to 5, the first extension surface 25 is parallel or substantially parallel to the first opposed surface 27. The second extension surface 35 is parallel or substantially parallel to the second opposed surface 37. Accordingly, in the example of FIGS. 2 to 5, both of the extension surfaces 25 and 35 become parallel or substantially parallel to the extension axis E1 of the end effector 5 when the treatment pieces 21 and 31 are closed to the minimum angle relative to each other.

The first inclined surface 26 is inclined to be closer to the side on which the first treatment piece 21 closes (the side of the arrow Y2) as a distance to the distal end (D1) of the first treatment piece 21 decreases. When the treatment pieces 21 and 31 are closed to the minimum angle, an inclination angle $\alpha 1$ of the first inclined surface 26 with respect to the direction along the extension axis E1 becomes equal to or substantially equal to half of the maximum opening angle θmax between the treatment pieces 21 and 31. In the present embodiment, in the range of extension of the first inclined surface 26, the first treatment piece 21 decreases in size in the direction in which the end effector 5 opens and closes, as a distance to the distal end (D1) of the first treatment piece 21 decreases. The size of the first treatment piece 21 in the direction in which the end effector 5 opens and closes is uniform or substantially uniform over the entire range of extension of the first extension surface 25 in the direction along the extension axis E1. The size of the first treatment piece 21 in the direction in which the end effector 5 opens and closes in the range of extension of the first inclined surface 26 is small, compared to the range of extension of the first extension surface 25 (range between the proximal end of the first treatment piece 21 and the proximal end of the first inclined surface 26 in the direction along the extension axis E1).

The second inclined surface 36 is inclined to be closer to the side on which the second treatment piece 31 closes (the side of the arrow Y1) as a distance to the distal end (D2) of the second treatment piece 31 decreases. When the treatment pieces 21 and 31 are closed to the minimum angle, an inclination angle α2 of the second inclined surface 36 with respect to the direction along the extension axis E1 becomes equal to or substantially equal to half of the maximum opening angle Amax between the treatment pieces 21 and 31. In the present embodiment, in the range of extension of the second inclined surface 36, the second treatment piece 31 decreases in size in the direction in which the end effector 5 opens and closes, as a distance to the distal end (D2) of the second treatment piece 31 decreases. The size of the second treatment piece 31 in the direction in which the end effector 5 opens and closes is uniform or substantially uniform over the entire range of extension of the second extension surface 35 in the direction along the extension axis E1. The size of the second treatment piece 31 in the direction in which the end effector 5 opens and closes is small in the range of extension of the second inclined surface 36, compared to the range of extension of the second extension surface 35 (range between the proximal end of the second treatment piece 31 and the proximal end of the second inclined surface 36 in the direction along the extension axis E1).

Since the inclination angles α1 and α2 are set as described above, when an opening angle between the treatment pieces 21 and 31 reaches the maximum opening angle θmax, a distance T between the inclined surfaces 26 and 36 in the direction in which the end effector 5 opens and closes becomes uniform or substantially uniform over the entire region in which the range of extension of the first inclined surface 26 and the range of extension of the second inclined surface 36 overlap in the direction along the extension axis E1 of the end effector 5. Thus, when the opening angle between the treatment pieces 21 and 31 reaches the maximum opening angle θmax, the inclined surfaces 26 and 36 become parallel or substantially parallel to each other. In the configuration in which the range of extension of the first inclined surface 26 and the range of extension of the second inclined surface 36 are identical or substantially identical to each other in the direction along the extension axis E1 of the end effector 5, when the opening angle between the treatment pieces 21 and reaches the maximum opening angle θmax, a distance T between the inclined surfaces 26 and 36 in the direction in which the end effector 5 opens and closes becomes uniform or substantially uniform over the entire range of extension of the first inclined surface 26 and the second inclined surface 36 in the direction along the extension axis E1 of the end effector 5.

Next, operations and effects of the dilator 2 and the treatment system 1 of the present embodiment will be described. In the present embodiment, the dilator 2 is used to perform a treatment in a narrowed part of the paranasal sinuses. In the description that follows, let us assume that the nasofrontal duct 12 between the frontal sinuses 11 and the nasal cavity 10 is an example of the narrowed part. It is to be noted that a treatment similar to the treatment that will be described below may be performed in a narrowed part of one of the frontal sinuses, the maxillary sinuses, the ethomoid sinuses, and the sphenoid sinuses, namely, in a narrowed part of one of the paranasal sinuses.

When a treatment is performed with the treatment system 1, the operator inserts the distal portion of the endoscope 3 into the nasal cavity 10, and observes the nasofrontal duct 12, which is a narrowed part, from the side of the nasal cavity 10. The nasofrontal duct 12 may be observed using an apparatus that generates an image by MRI or CT scanning, instead of the endoscope 3. Under observation by an observation apparatus such as the endoscope 3, a treatment of dilating the nasofrontal duct using the end effector 5 is performed. During the treatment of dilating the nasofrontal duct 12, the end effector 5 is allowed to pass through the nasal cavity 10, and is disposed at the nasofrontal duct (narrowed part) 12 of the frontal sinus (paranasal sinus) 11.

Figure 6:
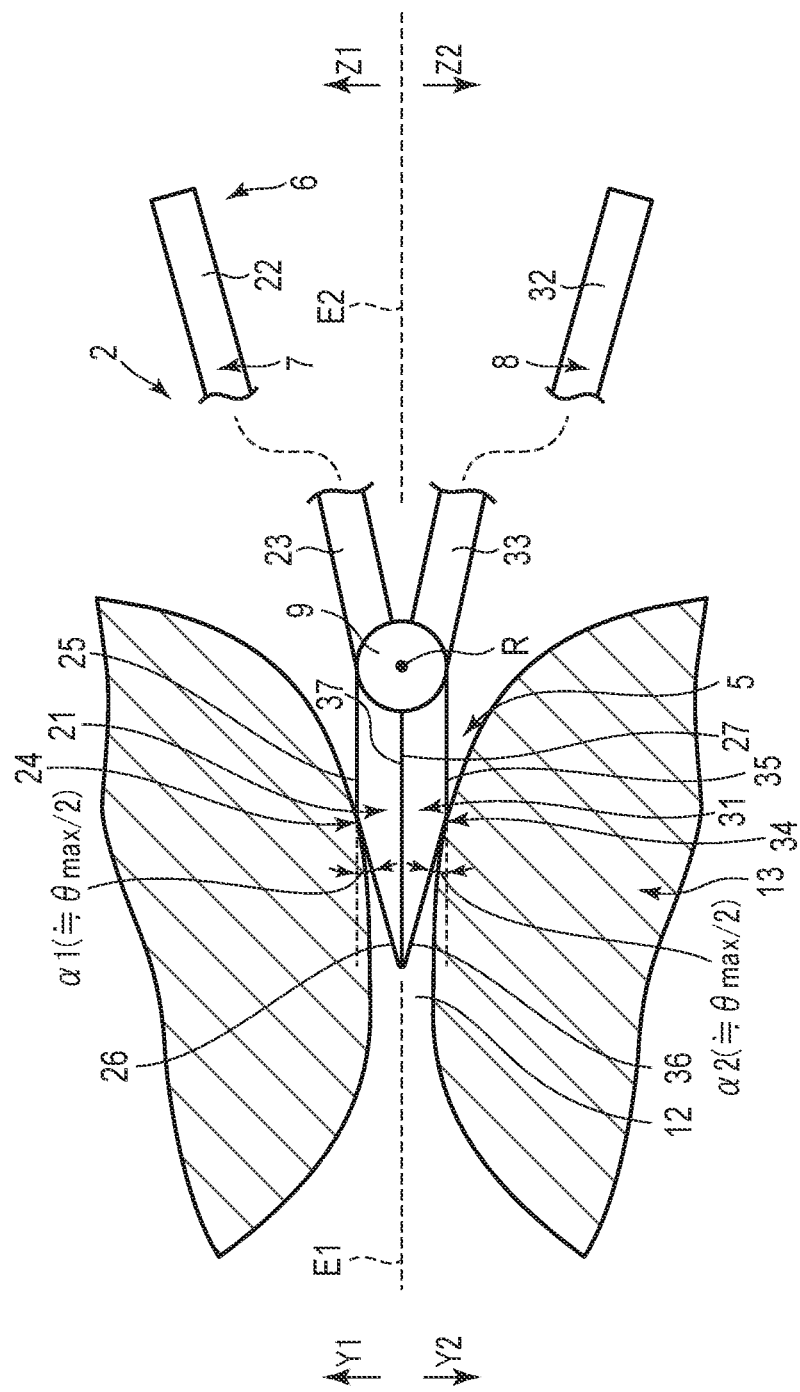
FIG. 6 is a schematic diagram showing an example of a state in which the end effector of the dilator according to the first embodiment is disposed in a nasofrontal duct.

FIG. 6 is a diagram showing an example of a state in which the end effector 5 of the dilator 2 is disposed in the nasofrontal duct 12, which is a narrowed part of the paranasal sinuses. As shown in FIG. 6, the end effector 5 is, for example, disposed in the nasofrontal duct 12 with the treatment pieces 21 and 31 closed. When the treatment pieces 21 and 31 are disposed in the nasofrontal duct 12, the operator adjusts the angular positions of the treatment pieces 21 and 31 in the circumferential direction of the nasofrontal duct (narrowed part) 12 by, for example, rotating the end effector 5 around the extension axis E1. Thereby, the direction in which the end effector 5 opens and closes in the nasofrontal duct 12 are adjusted. By the rotation of the end effector 5 around the extension axis E1 in the nasofrontal duct 12, the direction in which the end effector 5 opens and closes in the nasofrontal duct 12 are changed. The adjustment of the direction in which the end effector 5 opens and closes is performed with the treatment pieces 21 and 31 closed relative to each other.

Figure 7:
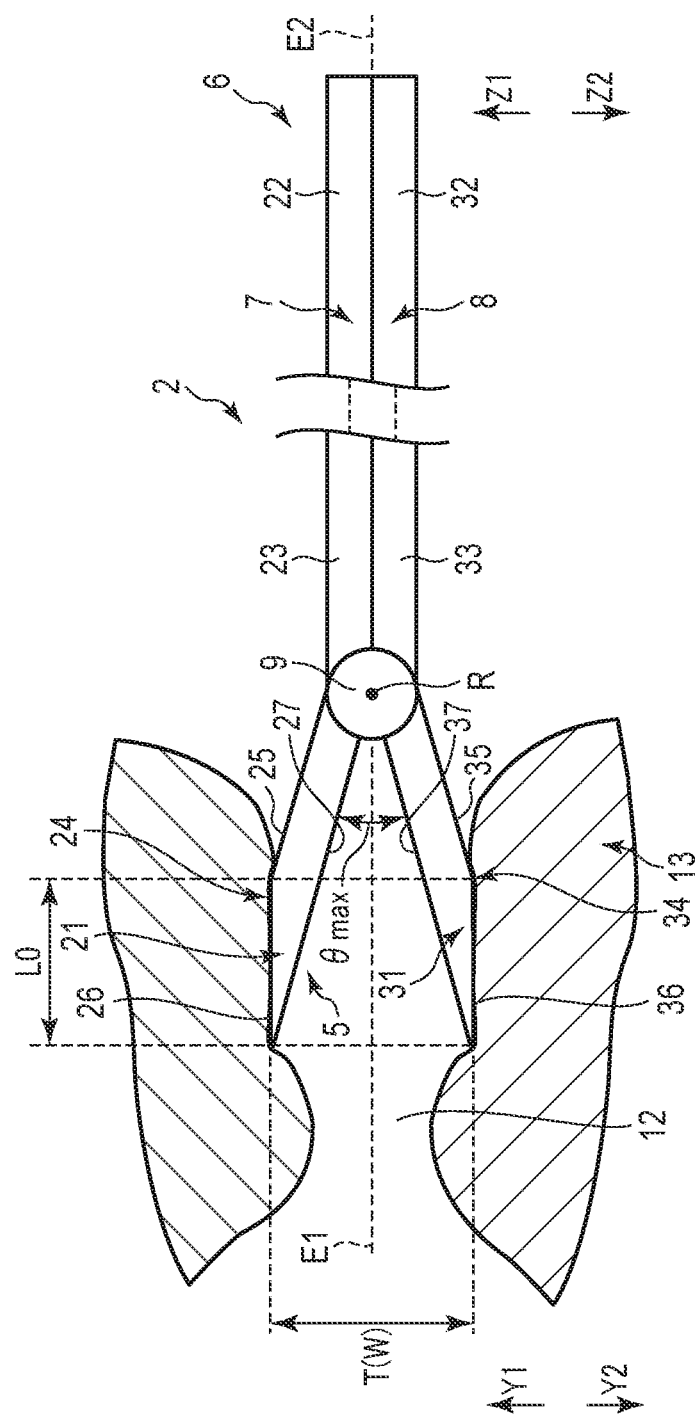
FIG. 7 is a schematic diagram showing an example of a state in which the treatment pieces according to the first embodiment are opened relative to each other, in such a manner that an opening angle between the treatment pieces reaches a maximum opening angle in the nasofrontal duct.

FIG. 7 shows an example of a state in which the treatment pieces 21 and 31 are opened relative to each other in the nasofrontal duct (narrowed part) 12, in such a manner that the opening angle θ between the treatment pieces 21 and 31 reaches the maximum opening angle θmax. As shown in FIG. 7, the operator closes, for example, the grips 22 and 32 relative to each other, with the direction in which the end effector 5 opens and closes adjusted in the nasofrontal duct 12. Thereby, the end effector 5 is configured in such a manner that the treatment pieces 21 and 31 are opened relative to each other, and the first inclined surface 26 of the first treatment piece 21 and the second inclined surface 36 of the second treatment piece 31 are made to abut tissues 13 forming the nasofrontal duct 12. At this time, the tissues 13 are pressed toward the side on which the first treatment piece 21 opens and the side on which the second treatment piece 31 opens in the nasofrontal duct (narrowed part) 12. The nasofrontal duct 12 is dilated by pressure from each of the treatment pieces 21 and 31. Since the treatment pieces 21 and 31 are opened relative to each other as the grips 22 and 32 are closed relative to each other, as described above, the operator can easily apply an operation force via the operating section 6 at the time of opening the treatment pieces 21 and 31 relative to each other. That is, the operator can easily perform the operation of opening the treatment pieces 21 and 31 relative to each other.

Figure 8:
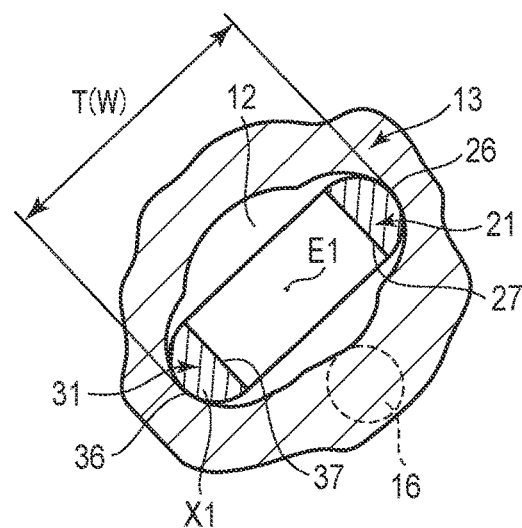
FIG. 8 is a schematic diagram showing an example of the nasofrontal duct immediately after dilation has been performed only once using the end effector at a circumferential position in a circumferential direction of the nasofrontal duct, according to the first embodiment.

FIG. 8 is a diagram showing an example of the nasofrontal duct (narrowed part) 12 immediately after dilation has been performed by the end effector 5 only once at a certain circumferential position X1 in a circumferential direction of the nasofrontal duct 12. FIG. shows a cross section perpendicular or substantially perpendicular to the direction in which the nasofrontal duct 12 extends. In the dilation by the end effector 5, the nasofrontal duct 12 is dilated only in the direction in which the end effector 5 opens and closes, as shown in FIG. 8. That is, even when the treatment pieces 21 and 31 are opened relative to each other in the nasofrontal duct 12, the nasofrontal duct 12 is not dilated in the direction intersecting the extension direction of the nasofrontal duct 12 and intersecting the direction in which the end effector 5 opens and closes. Accordingly, the nasofrontal duct 12 is anisotropically dilated by the treatment using the dilator 2.

Figure 9:
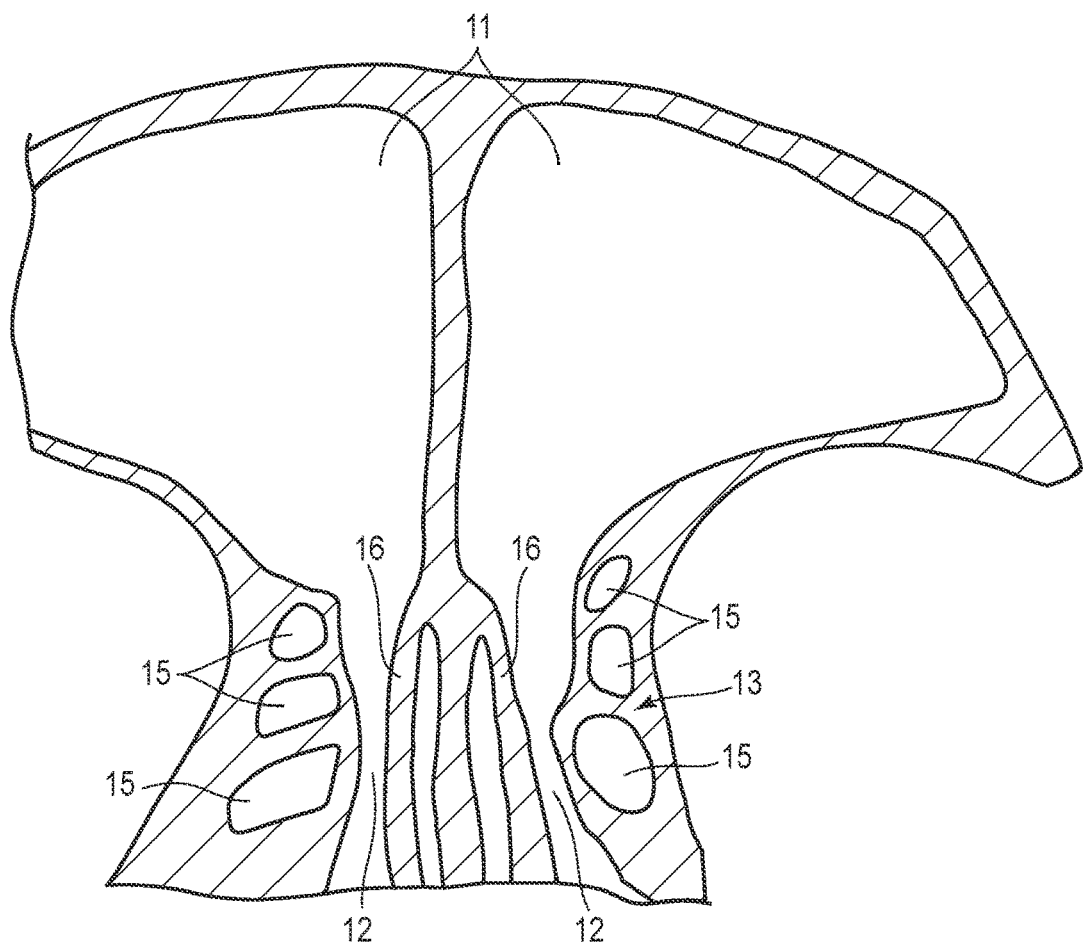
FIG. 9 is a schematic diagram showing an example of frontal sinuses, a nasofrontal duct between a nasal cavity and the frontal sinuses, and the vicinity thereof.

FIG. 9 is a diagram showing an example of the frontal sinuses 11, which are one of the paranasal sinuses, the nasofrontal duct 12 between the nasal cavity 10 and the frontal sinuses 11, and the vicinity thereof. As shown in FIG. 9, the nasofrontal duct 12 is formed by tissues 13 such as a cellulitis 15 and the middle nasal concha 16. Accordingly, the cellulitis 15 and the middle nasal concha 16 are present in the vicinity of the nasofrontal duct 12. During the dilation of the nasofrontal duct 12, it is required that the nasofrontal duct 12 be dilated without exertion of an excessive pressure on the middle nasal concha 16 in the vicinity of the nasofrontal duct 12, and without deformation of the middle nasal concha 16. At the time of dilation of a narrowed part of the paranasal sinuses other than the nasofrontal duct 12, there is a case where it is required that an excessive pressure not be exerted on a specific portion in the vicinity of the narrowed part in the tissues, and that the specific portion not be deformed by the dilation of the narrowed part.

In the treatment using the dilator 2 of the present embodiment, the angular positions of the treatment pieces and 31 in the circumferential direction of the nasofrontal duct 12 are adjusted, prior to the dilation of the nasofrontal duct 12, in such a manner that the treatment pieces 21 and 31 are separated from the middle nasal concha (specific portion) 16 in the circumferential direction of the nasofrontal duct 12. For example, at the circumferential position X1 at which dilation has been performed in FIG. 8, the treatment pieces 21 and 31 are located at angular positions deviated from the middle nasal concha 16 in the circumferential direction of the nasofrontal duct 12. Since the nasofrontal duct 12 is dilated with the treatment pieces 21 and 31 separated from the middle nasal concha 16 in the circumferential direction of the nasofrontal duct 12, the nasofrontal duct 12 is dilated without exertion of an excessive pressure on the middle nasal concha 16 and without deformation of the middle nasal concha 16. When a narrowed part other than the nasofrontal duct 12 is dilated, the angular positions of the treatment pieces 21 and 31 in the circumferential direction of the narrowed part are adjusted in such a manner that the treatment pieces 21 and 31 are separated from a specific portion in the circumferential direction of the narrowed part, similarly to the dilation of the nasofrontal duct 12. Thereby, it is possible to dilate the narrowed part without exerting an excessive pressure on the specific portion in the vicinity of the narrowed part, and without deforming the specific portion. That is, the direction in which the narrowed part (e.g., 12) is dilated becomes selectable, allowing the narrowed part (e.g., 12) to be dilated only in the direction in which the dilation should be induced.

In the treatment using the dilator 2 of the present embodiment, both the adjustment of the direction in which the end effector 5 opens and closes in the nasofrontal duct 12, and the dilation of the nasofrontal duct 12 with the direction in which the end effector 5 opens and closes adjusted are repeatedly performed multiple times. That is, after the treatment pieces 21 and 31 are opened relative to each other to dilate the nasofrontal duct 12, the operator rotates the end effector 5 around the extension axis E1 to change, from the state in which the dilation has been performed, the angular positions of the treatment pieces 21 and 31 in the circumferential direction of the nasofrontal duct 12. At this time, the end effector 5 is rotated with the treatment pieces 21 and 31 closed relative to each other. Subsequently, after the angular positions of the treatment pieces 21 and 31 in the circumferential direction of the nasofrontal duct 12 are changed, the treatment pieces 21 and 31 are opened relative to each other to dilate the nasofrontal duct 12, with the treatment pieces 21 and 31 located at the changed angular positions.

Figure 10:
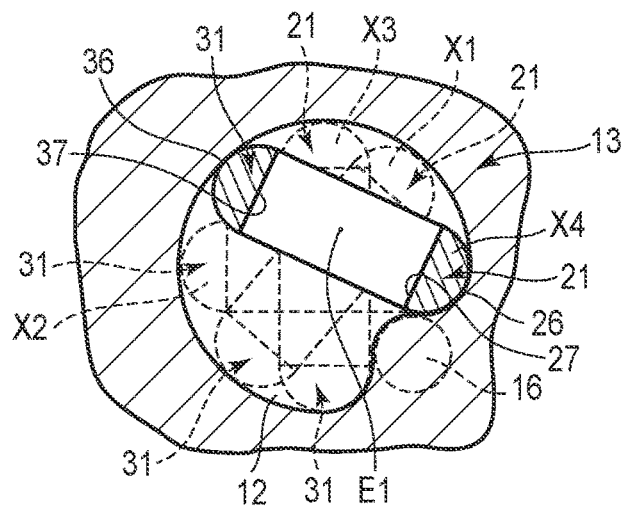
FIG. 10 is a schematic diagram showing an example of the nasofrontal duct immediately after dilation has been performed at multiple circumferential positions in the circumferential direction of the nasofrontal duct using the end effector, according to the first embodiment.

FIG. 10 is a diagram showing an example of the nasofrontal duct (narrowed part) 12 immediately after dilation has been performed by the end effector 5 at multiple (four in the example of FIG. 10) circumferential positions X1 to X4 in the circumferential direction of the nasofrontal duct 12. FIG. 10 shows a cross section perpendicular or substantially perpendicular to the direction in which the nasofrontal duct 12 extends. In the example of FIG. 10, the nasofrontal duct 12 is dilated in the order of the circumferential positions X1, X2, X3, and X4, and the state immediately after the dilation at the circumferential position X4 has been performed is shown. At the circumferential positions X1 to X4 in FIG. 10, the angular positions of the treatment pieces 21 and 31 in the circumferential direction of the nasofrontal duct 12 are different from each other, and the direction in which the end effector 5 opens and closes in the nasofrontal duct 12 are different from each other. In the treatment using the dilator 2, when adjustment of the direction in which the end effector 5 opens and closes is performed after dilation of the nasofrontal duct (narrowed part) 12 is performed one or more times, the angular positions of the treatment pieces 21 and 31 in the circumferential direction of the nasofrontal duct 12 are adjusted in such a manner that the direction in which the end effector 5 opens and closes become different from that in the dilations already performed. Thus, in the example of FIG. 10, after dilation is performed at, for example, the circumferential position X3, the end effector 5 is adjusted to be at the circumferential position X4 at which the direction in which the end effector 5 opens and closes are different from that at the circumferential positions X1 to X3 at which dilations have already been performed. Subsequently, at the circumferential position X4 at which the angular positions of the treatment pieces 21 and 31 are different from the circumferential positions X1 to X3 at which dilation has already been performed, the treatment pieces 21 and 31 are opened relative to each other, and the nasofrontal duct (narrowed part) 12 is dilated.

Even when the nasofrontal duct 12 is dilated multiple times during the treatment, every dilation is performed with the treatment pieces 21 and 31 separated from the middle nasal concha (specific portion) 16 in the circumferential direction of the nasofrontal duct 12. In the example of FIG. 10, the treatment pieces 21 and 31 are located at angular positions deviated from the middle nasal concha (specific portion) 16 in the circumferential direction of the nasofrontal duct 12, at any of the circumferential positions X1 to X4. Accordingly, even when dilatation is performed multiple times in the nasofrontal duct 12, every dilation is performed in such a manner that the nasofrontal duct 12 is dilated without exertion of an excessive pressure on the middle nasal concha (specific portion) 16 and without deformation of the middle nasal concha 16.

In the present embodiment, each of the inclination angle $\alpha 1$ of the first inclined surface 26 and the inclination angle $\alpha 2$ of the second inclined surface 36 is equal to or substantially equal to half of the maximum opening angle Amax between the treatment pieces 21 and 31, and the inclined surfaces 26 and 36 become parallel or substantially parallel to each other when the opening angle between the treatment pieces 21 and 31 reaches the maximum opening angle $\theta max$. When the opening angle between the treatment pieces 21 and 31 reaches the maximum opening angle $\theta max$, a distance T between the inclined surfaces 26 and 36 in the direction in which the end effector 5 opens and closes becomes uniform or substantially uniform over the entire region in which the range of extension of the first inclined surface 26 and the range of extension of the second inclined surface 36 overlap in the direction along the extension axis E1 of the end effector 5. Thus, in the treatment using the dilator 2, by opening the treatment pieces 21 and 31 relative to each other until the maximum opening angle $\theta max$ is reached, a dilation width W between a portion at which the first inclined surface 26 abuts the tissues 13 and a portion at which the second inclined surface 36 abuts the tissues 13 becomes uniform or substantially uniform, over the entire region in which the range of extension of the first inclined surface 26 and the range of extension of the second inclined surface 36 overlap, in the direction along the extension axis E1 of the end effector 5. That is, by opening the treatment pieces 21 and 31 relative to each other until the maximum opening angle $\theta max$ is reached, the dilation width W becomes uniform or substantially uniform over a predetermined length L0 in the direction along the extension axis E1. In the treatment using the dilator 2, since the dilation width W can be made uniform or substantially uniform over the predetermined length L0, as described above, the efficiency of treatment is improved.

As described above, in the configuration in which the range of extension of the first inclined surface 26 and the range of extension of the second inclined surface 36 are identical or substantially identical to each other in the direction along the extension axis E1 of the end effector 5, when the opening angle between the treatment pieces 21 and reaches the maximum opening angle $\theta max$, a distance T between the inclined surfaces 26 and 36 in the direction in which the end effector 5 opens and closes becomes uniform or substantially uniform over the entire range of extension of the inclined surfaces 26 and 36 in the direction along the extension axis E1 of the end effector 5. In this case, by opening the treatment pieces 21 and 31 relative to each other until the maximum opening angle $\theta max$ is reached, the dilation width W between the portion at which the first inclined surface 26 abuts the tissues 13 and the portion at which the second inclined surface 36 abuts the tissues 13 becomes uniform or substantially uniform, over the entire range of extension of the inclined surfaces 26 and 36 the direction along the extension axis E1 of the end effector 5.

(Modification)

Figure 11:
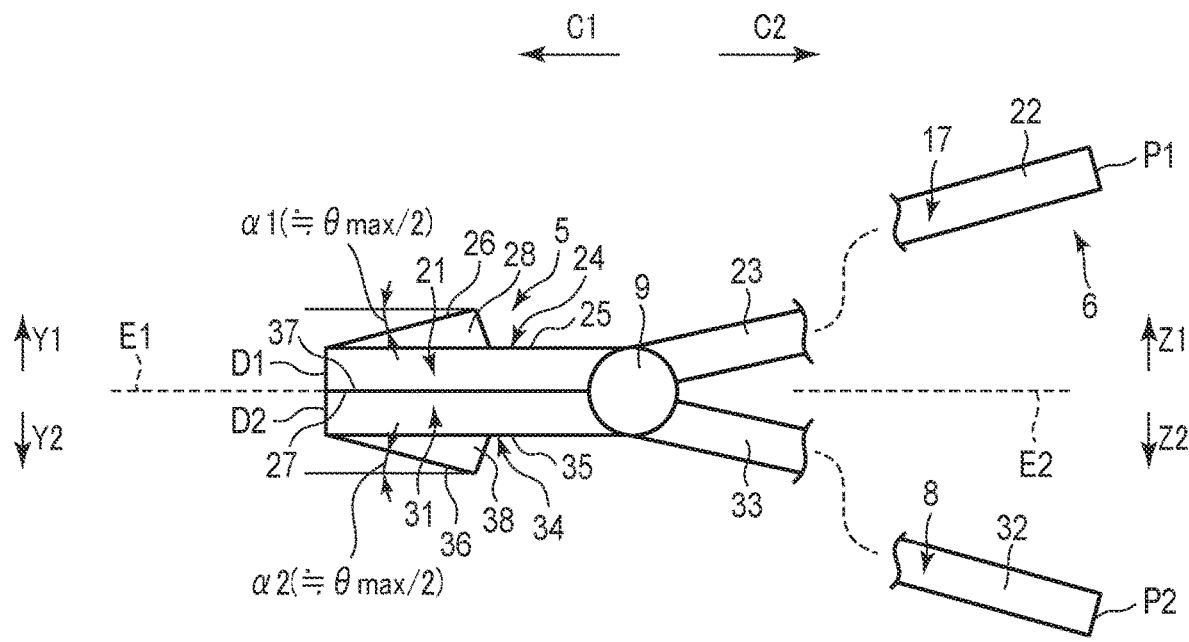
FIG. 11 is a schematic diagram showing a dilator according to a first modification in a state in which treatment pieces are closed to a minimum angle.
Figure 12:
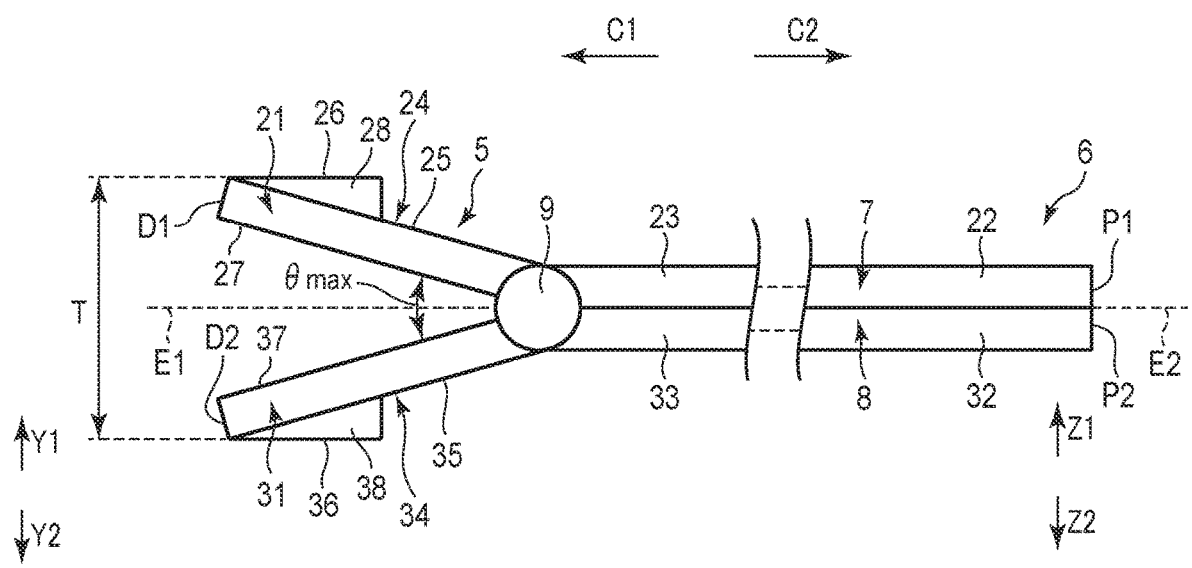
FIG. 12 is a schematic diagram showing the dilator according to the first modification in a state in which the treatment pieces are opened to a maximum angle.

In a first modification shown in FIGS. 11 and 12, a first projection 28 projecting toward the side on which a first treatment piece 21 opens is provided on a first treatment surface 24 of a first treatment piece 21, and a second projection 38 projecting toward the side on which a second treatment piece 31 opens is provided on a second treatment surface 34 of a second treatment piece 31. In the present modification, a first inclined surface 26 is provided in the first projection 28, and a second inclined surface 36 is provided in the second projection 38. In the present modification, a first extension surface 25 is continuous with a proximal side of the first projection 28, and a second extension surface 35 is continuous with a proximal side of the second projection 38. In the present modification, too, both of the opposed surfaces 27 and 37 and both of the extension surfaces 25 and 35 become parallel or substantially parallel to the extension axis E1 of the end effector 5 when the treatment pieces 21 and 31 are closed to the minimum angle relative to each other. In the present modification, too, the first inclined surface 26 is inclined to be closer to the side on which the first treatment piece 21 closes (the side of the arrow Y2) as a distance to the distal end (D1) of the first treatment piece 21 decreases. An inclination angle $\alpha 1$ of the first inclined surface 26 with respect to the direction along the extension axis E1 when the treatment pieces 21 and 31 are closed to the minimum angle becomes equal to or substantially equal to half of the maximum opening angle $\theta max$ between the treatment pieces 21 and 31. The second inclined surface 36 is inclined to be closer to the side on which the second treatment piece 31 closes (the side of the arrow Y1) as a distance to the distal end (D2) of the second treatment piece 31 decreases. An inclination angle $\alpha 2$ of the second inclined surface 36 with respect to the direction along the extension axis E1 when the treatment pieces 21 and 31 are closed to the minimum angle becomes equal to or substantially equal to half of the maximum opening angle $\theta max$ between the treatment pieces 21 and 31.

However, in the present modification, since the first inclined surface 26 is provided on the first projection 28, the first inclined surface 26 projects toward the side on which the first treatment piece 21 opens, compared to portions of the first treatment surface 24 other than the first inclined surface 26. Thus, in the present modification, the size of the first treatment piece 21 in the direction in which the end effector 5 opens and closes is large in the range of extension of the first inclined surface 26, compared to the range of extension of the first extension surface 25 (the range between the proximal end of the first treatment piece 21 and the proximal end of the first inclined surface 26 in the direction along the extension axis E1). Similarly, in the present modification, since the second inclined surface 36 is provided on the second projection 38, the second inclined surface 36 projects greatly toward the side on which the second treatment piece 31 opens, compared to a portion of the second treatment surface 34 other than the second inclined surface 36. Thus, in the present modification, the size of the second treatment piece 31 in the direction in which the end effector 5 opens and closes is large in the range of extension of the second inclined surface 36, compared to the range of extension of the second extension surface 35 (the range between the proximal end of the second treatment piece 31 and the proximal end of the second inclined surface 36 in the direction along the extension axis E1). According to the present modification, it is possible to produce operations and effects similar to those of the first embodiment.

Figure 13:
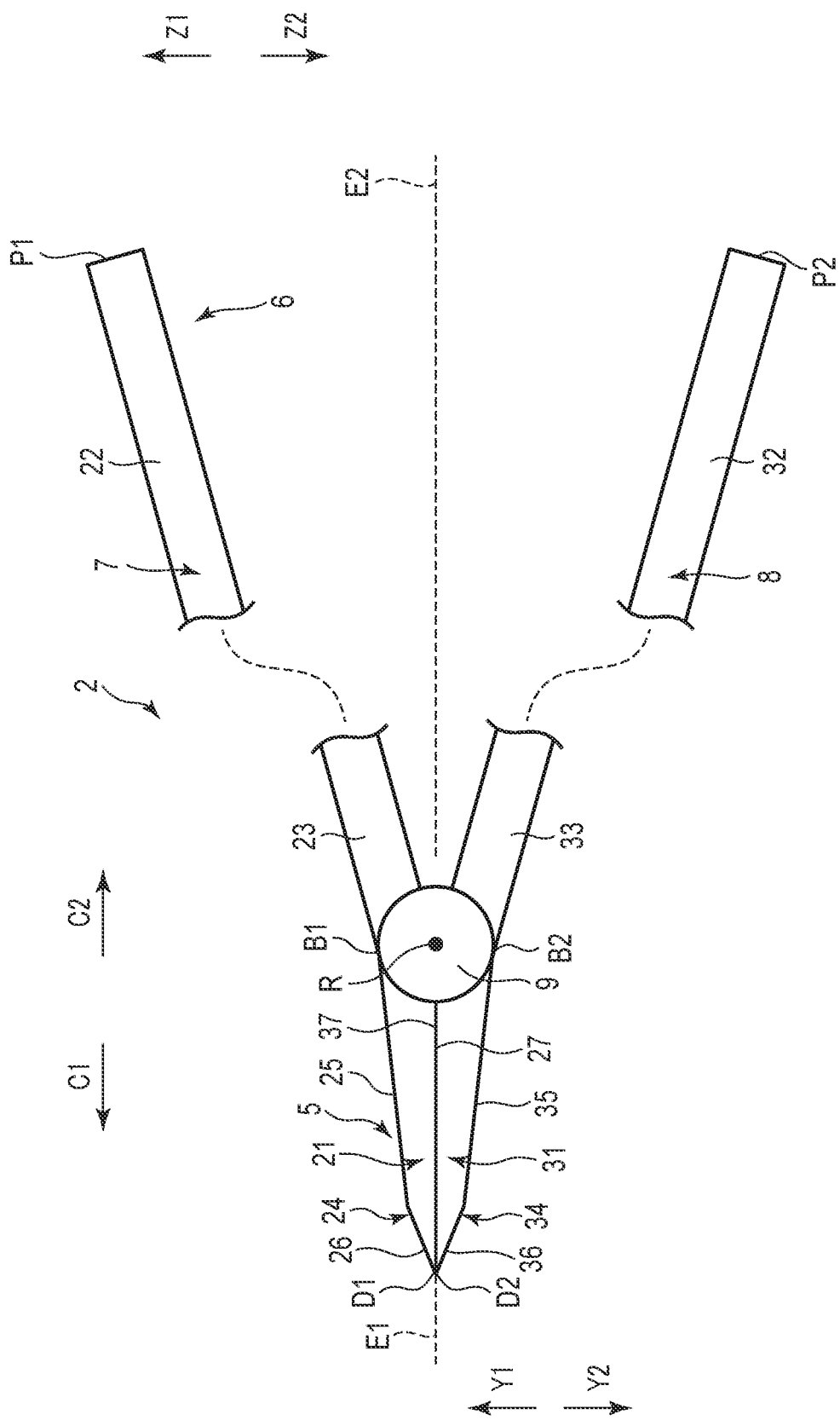
FIG. 13 is a schematic diagram showing a dilator according to a second modification in a state in which the treatment pieces are closed to a minimum angle.

In the second modification shown in FIGS. 13 and 14, the first extension surface 25 is not parallel or substantially parallel to the first opposed surface 27. The second extension surface 35 is not parallel or substantially parallel to the second opposed surface 37. Thus, in the present modification, when the treatment pieces 21 and 31 are closed to the minimum angle relative to each other, neither of the extension surfaces 25 and 35 is parallel or substantially parallel to the extension axis E1 of the end effector 5. However, in the present modification, too, both of the opposed surfaces 27 and 37 become parallel or substantially parallel to the extension axis E1 of the end effector 5 when the treatment pieces 21 and 31 are closed to the minimum angle relative to each other. In the present modification, too, the first inclined surface 26 is inclined to be closer to the side on which the first treatment piece 21 closes (the side of the arrow Y2) as a distance to the distal end (D1) of the first treatment piece 21 decreases. The second inclined surface 36 is inclined to be closer to the side on which the second treatment piece 31 closes (the side of the arrow Y1) as a distance to the distal end (D2) of the second treatment piece 31 decreases. In the present modification, too, the inclined surfaces 26 and 36 become parallel or substantially parallel to each other when the opening angle between the treatment pieces 21 and 31 reaches the maximum opening angle θmax, as described above, and it is thereby possible to produce operations and effects similar to those of the first embodiment.

In a modification, at least one of the opposed surfaces 27 and 37 is formed in an uneven shape. In another modification, at least one of a projection on the first opposed surface 27 projecting toward the second opposed surface 37 and a projection on the second opposed surface projecting toward the first opposed surface 27 is provided. In these modifications, too, the inclined surfaces 26 and 36 become parallel or substantially parallel to each other when the opening angle between the treatment pieces 21 and 31 reaches the maximum opening angle θmax. Therefore, according to these modifications, it is possible to produce the same operations and effects as those of the first embodiment.

In the above-described embodiment and the like, a dilator (2) that dilates a narrowed part (12) of a paranasal sinus (11) includes an end effector (5), and the end effector (5) includes paired treatment pieces (21, 31) that are openable and closable relative to each other. Each of the treatment pieces (21 and 31) includes a treatment surface (24; 34) facing a side (Y1; Y2) on which it opens, and each of the treatment surfaces (24 and 34) includes an inclined surface (26; 36) inclined to be closer to a side on which the treatment piece (21; 31) closes as a distance to a distal end (D1; D2) of the treatment piece (21; 31) decreases. When the paired treatment pieces are opened to the maximum angle relative to each other, the paired inclined surfaces (26; 36) become parallel or substantially parallel to each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dilator that dilates a narrowed part of a paranasal sinus, the dilator comprising:
   an end effector extending along an extension axis from a proximal side toward a distal side, the end effector including a first treatment piece and a second treatment piece that is openable and closable relative to the first treatment piece;
   a first treatment surface provided on the first treatment piece and facing a side on which the first treatment piece opens;
   a second treatment surface provided on the second treatment piece and facing a side on which the second treatment piece opens;
   a first inclined surface provided on a distal most end of the first treatment surface, the first inclined surface being inclined such that a first distance from the extension axis to the first inclined surface decreases in a distal direction; and
   a second inclined surface provided on a distal most end of the second treatment surface, the second inclined surface being inclined such that a second distance from the extension axis to the second inclined surface decreases in a distal direction, and the second inclined surface becoming parallel to the first inclined surface when the first treatment piece and the second treatment piece are opened to a maximum angle relative to each other.

2. The dilator according to claim 1, wherein
   the end effector forms a maximum opening angle between the first treatment piece and the second treatment piece when the first treatment piece and the second treatment piece are opened to the maximum angle relative to each other,
   an inclination angle of the first inclined surface is equal to half of the maximum opening angle, and
   an inclination angle of the second inclined surface is equal to half of the maximum opening angle.

3. The dilator according to claim 1, further comprising:
   a rotatable joint which couples the first treatment piece and the second treatment piece so as to be openable and closable relative to each other; and
   a grip provided farther from the end effector than the rotatable joint, and to which an operation to open or close the first treatment piece and the second treatment piece relative to each other is input.

4. The dilator according to claim 3, wherein the grip includes:
   a first grip to which an operation force to move the first treatment piece is applied; and
   a second grip which is openable and closable relative to the first grip, and to which an operation force to move the second treatment piece is applied, and
   the first treatment piece and the second treatment piece are opened relative to each other as the first grip and the second grip of the grip are closed relative to each other.

5. The dilator according to claim 4, wherein a direction in which the grip opens and closes through a movement of opening and closing the first grip and the second grip relative to each other is parallel to a direction in which the end effector opens and closes.

6. The dilator according to claim 1, wherein a range of extension of the first inclined surface is identical to a range of extension of the second inclined surface in a direction along the extension axis.

7. The dilator according to claim 1, wherein the first treatment surface faces a side opposite to the second treatment surface.

8. The dilator according to claim 1, wherein moving directions of the first and second treatment piece are separated from each other by 180 degrees in a direction around the extension axis of the end effector when the end effector opens and closes.

9. The dilator according to claim 1, wherein the first and second treatment surfaces are surfaces configured to be in contact with a tissue in paranasal sinus, and out of contact with a middle nasal concha.

10. A treatment system comprising:
the dilator according to claim 1; and
an observation apparatus configured to observe the narrowed part of the paranasal sinus.

11. The treatment system according to claim 10, wherein the observation apparatus includes an endoscope configured to, when inserted into a nasal cavity, observe the narrowed part of the paranasal sinus from a side of the nasal cavity.

12. A method of dilating a narrowed part of a paranasal sinus using a dilator, the method comprising:
allowing an end effector of the dilator, which extends along an extension axis, to pass through a nasal cavity and disposing the end effector in the narrowed part of the paranasal sinus;
adjusting angular positions of a first treatment piece and a second treatment piece of the end effector in a circumferential direction of the narrowed part, with the end effector disposed in the narrowed part, and adjusting a direction offset from the extension axis in which the end effector opens and closes in the narrowed part through a movement of opening and closing the first treatment piece and the second treatment piece relative to each other; and
opening the first treatment piece and the second treatment piece relative to each other such that a first inclined surface provided on a distal most end of the first treatment piece and a second inclined surface provided on a distal most end of the second treatment piece, are parallel to each other and open in the direction offset from the extension axis to dilate the narrowed part in the direction offset from the extension axis.

13. The dilating method according to claim 12, wherein both adjustment of the direction in which the end effector opens and closes and dilation of the narrowed part with the direction in which the end effector opens and closes adjusted are repeatedly performed multiple times, and the adjustment of the direction in which the end effector opens and closes after the dilation of the narrowed part is performed multiple times includes adjusting the angular positions of the first treatment piece and the second treatment piece in the circumferential direction of the narrowed part.

14. The dilating method according to claim 12, wherein adjustment of the direction in which the end effector opens and closes includes adjusting the angular positions of the first treatment piece and the second treatment piece in the circumferential direction of the narrowed part, in such a manner that the first treatment piece and the second treatment piece are separated from a specific portion in a vicinity of the narrowed part in the circumferential direction of the narrowed part.

15. The dilating method according to claim 14, wherein the dilation of the narrowed part with the direction in which the end effector opens and closes adjusted includes dilating a nasofrontal duct between a frontal sinus and a nasal cavity, and
the adjustment of the direction in which the end effector opens and closes includes adjusting the angular positions of the first treatment piece and the second treatment piece in the circumferential direction of the nasofrontal duct, in such a manner that the first treatment piece and the second treatment piece are separated from a middle nasal concha in the circumferential direction of the nasofrontal duct.

16. The dilating method according to claim 12, wherein the end effector of the dilator forms a maximum opening angle between the first treatment piece and the second treatment piece when the first treatment piece and the second treatment piece are opened to the maximum opening angle relative to each other, and
dilation of the narrowed part with the direction in which the end effector opens and closes adjusted includes opening the first treatment piece and the second treatment piece relative to each other until the maximum opening angle is reached, with the first inclined surface and the second inclined surface abutting the tissues in the narrowed part, thereby making a dilation width between a portion at which the first inclined surface abuts tissues and a portion at which the second inclined surface abuts the tissues uniform, over an entire region in which a range of extension of the first inclined surface and a range of extension of the second inclined surface overlap in a direction along the extension axis of the end effector.

17. The dilating method according to claim 16, wherein the range of extension of the first inclined surface is identical to the range of extension of the second inclined surface, in the direction along the extension axis of the end effector, and
the dilation of the narrowed part with the direction in which the end effector opens and closes adjusted includes making the dilation width between the portion at which the first inclined surface abuts the tissues and the portion at which the second inclined surface abuts the tissues uniform, over the entire ranges of extension of the first inclined surface and the second inclined surface in the direction along the extension axis of the end effector.

18. The dilating method according to claim 12, wherein the dilator includes a rotatable joint which couples the first treatment piece and the second treatment piece so as to be openable and closable relative to each other, a first grip provided farther from the end effector than the rotatable joint, and a second grip provided farther from the end effector than the rotatable joint so as to be openable and closable relative to the first grip, and
the dilation of the narrowed part with the direction in which the end effector opens and closes adjusted includes opening the first treatment piece and the second treatment piece relative to each other as the first grip and the second grip are closed relative to each other.

19. The dilating method according to claim 12, further comprising:
an observation apparatus that is an endoscope; and
the dilating method comprising inserting the endoscope into the nasal cavity, and observing the narrowed part of the paranasal sinus with the endoscope from a side of the nasal cavity.

20. The dilating method according to claim 19, wherein the endoscope is inserted from an external nostril and allowed to pass through the nasal cavity.

21. The dilating method according to claim 12, wherein the end effector is inserted from an external nostril and allowed to pass through the nasal cavity.

* * * * *